US011937893B2

(12) United States Patent
Robinson et al.

(10) Patent No.: US 11,937,893 B2
(45) Date of Patent: Mar. 26, 2024

(54) SYSTEMS AND METHODS FOR LIGHT DEACTIVATION AND REMOVAL OF LIGHT DEACTIVATED ADHESIVE DRAPES

(71) Applicant: KCI LICENSING, INC., San Antonio, TX (US)

(72) Inventors: Timothy Mark Robinson, Wimborne (GB); Christopher Brian Locke, Bournemouth (GB); Justin Alexander Long, Lago Vista, TX (US); Ashwatha Price, Wimborne (GB)

(73) Assignee: 3M Innovative Properties Company, Saint Paul, MN (US)

(*) Notice: Subject to any disclaimer, the term of this patent is extended or adjusted under 35 U.S.C. 154(b) by 513 days.

(21) Appl. No.: 17/259,496

(22) PCT Filed: Jul. 18, 2019

(86) PCT No.: PCT/US2019/042321
§ 371 (c)(1),
(2) Date: Jan. 11, 2021

(87) PCT Pub. No.: WO2020/018735
PCT Pub. Date: Jan. 23, 2020

(65) Prior Publication Data
US 2021/0267705 A1 Sep. 2, 2021

Related U.S. Application Data

(60) Provisional application No. 62/699,864, filed on Jul. 18, 2018.

(51) Int. Cl.
*A61B 46/00* (2016.01)
*A61B 46/20* (2016.01)
(Continued)

(52) U.S. Cl.
CPC .............. *A61B 46/20* (2016.02); *A61B 46/40* (2016.02); *C09J 7/30* (2018.01); *C09J 7/403* (2018.01);
(Continued)

(58) Field of Classification Search
CPC ... A61B 46/20; A61B 46/40; A61B 2046/205; C09J 7/30; C09J 7/403; C09J 2301/502;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion on International Patent Application No. PCT/US2019/042321 dated Oct. 21, 2019 (13 pages).
(Continued)

*Primary Examiner* — Camtu T Nguyen

(57) ABSTRACT

Provided herein is a system and method for mitigating premature light deactivation of light deactivated adhesive drapes. One aspect provides a system comprising a drape, a photosensitive adhesive layer, a release agent, and an optical fiber mesh layer configured as a light pipe, where the system is adapted to be coupled to a tissue site and released therefrom upon or after exposure to an external stimulus such as certain wavelengths of light. Another aspect includes a pipe light pipe, as an alternative to the optical fiber mesh layer. The systems may have a removable blocking layer to
(Continued)

prevent the photosensitive adhesive from being exposed to deactivation wavelengths prematurely. Another aspect provides a method for application and removal of a drape using the light pipe to transport or route light to the drape to deactivate the photosensitive adhesive layer and promote easy, clean, and less painful removal of the drape.

23 Claims, 10 Drawing Sheets

(51) Int. Cl.
C09J 7/30 (2018.01)
C09J 7/40 (2018.01)

(52) U.S. Cl.
CPC ... *A61B 2046/205* (2016.02); *C09J 2301/502* (2020.08)

(58) Field of Classification Search
CPC .............. A61F 13/0216; A61F 13/0266; A61F 13/0269; A61F 13/0253; A61F 2013/00289
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,161,176 A | 7/1979 | Harris et al. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,489,279 A | 2/1996 | Meserol | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2009/0204084 A1* | 8/2009 | Blott .................. A61M 3/022 604/290 |
| 2009/0216170 A1 | 8/2009 | Robinson et al. | |
| 2017/0232161 A1 | 8/2017 | Fewkes et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |

(56) References Cited

FOREIGN PATENT DOCUMENTS

| GB | 2 333 965 A | 8/1999 |
|---|---|---|
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2005/046760 A1 | 5/2005 |
| WO | WO-2017/151226 A1 | 9/2017 |
| WO | WO-2018/002817 A1 | 1/2018 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C.® Therapy Clinical Guidelines: A Reference Source for Clinicians; Jul. 2007.

* cited by examiner

SYSTEMS AND METHODS FOR LIGHT DEACTIVATION AND REMOVAL OF LIGHT DEACTIVATED ADHESIVE DRAPES

CROSS-REFERENCE TO RELATED APPLICATIONS

This application claims priority to and the benefit of international patent application number PCT/US2019/042321, filed Jul. 18, 2019, which claims priority to and the benefit of U.S. Provisional Application No. 62/699,864, filed Jul. 18, 2018, the complete contents of which are both incorporated into the present application by reference.

BACKGROUND

1. Field of Invention

The present application relates generally to the field of tissue treatment, and more specifically to a system and method for facilitating the application and removal of a drape from a tissue site.

2. Description of Related Art

Systems and devices currently exist for the treatment of tissue, such as wound tissue and skin tissue. Some current tissue treatment systems require the use of an adhesive drape to secure all or a portion of the tissue treatment system to a tissue site. For example, an adhesive drape can be used to secure a gauze portion of a bandage to a wound site by adhering to the skin or other tissue surrounding the wound. Drapes intended for use with negative pressure wound therapy (NPWT) have certain desirable characteristics. Some of these characteristics are that the drape is easy to apply, doesn't adhere well to itself if folded (e.g., adhesive to adhesive) upon application to tissue, achieves a good seal with the tissue, adheres well to tissue and to its film (e.g., polyurethane) covering when layered or overlapped, enables atraumatic removal, is highly breathable, is repositionable upon application, and achieves adhesion that is not affected by patient heat or sweat.

SUMMARY

Certain light sensitive or light deactivated adhesive drape systems have been proposed to allow easier removal of the drape system from a patient. Some of these light sensitive or light deactivated adhesive drape systems are sensitive to UV or visible light. These drapes are effective at maintaining a seal until they were exposed to UV or visible light. The UV or visible light would deactivate the adhesive tack of the drape system by crosslinking the adhesive so that it irreversibly transformed the adhesive composition from a viscoelastic state to an elastic state. These drapes enable a high-bond strength adhesive dressing with trauma-free removal that utilizes a light sensitive skin adhesive and is protected from light deactivation (UV or visible light) by a light blocking/opaque film.

However in certain larger embodiments, such as a back or sacral dressing, or in patients with larger dressing areas, it may be quite inconvenient or time-consuming to remove the dressing without turning the patient over for a certain length of time (e.g., about 5 minutes) for the light sensitive skin adhesive to deactivate. This task may be strenuous for both the caregiver and the patient, especially for patients who are elderly, weak, or have traumatic wounds. The disclosed embodiments describe systems and methods that facilitate the easy light deactivation of larger area light sensitive skin adhesive dressings to minimize the need to turn or roll the patient prior to removal of dressing.

In some embodiments, these drapes can be used with a compact, low power system where battery power and efficiency is key to the duration of therapy. In these embodiments, it is imperative that such a dressing be applied and seal with no or very low leakage. Any leak which results in a pressure drop of more than 1 cc/min may result in a leak alarm and the suspension of therapy. To remedy this possibility, the dressing maybe designed with materials that can enable it to achieve an adequate seal around the wound site. This may be achieved with a combination of adhesive features, such as a combination of a very strong adhesive having a high bond strength with a dressing that is very thick and conformable for the patient. However, while this combination may excel at reducing or eliminating leakage, it may result in a dressing that can be very painful for dressing removal and may result in damage to delicate or damaged skin. A switchable adhesive where the user is required to use a separate tool to trigger the release of the dressing can address many of these issues but these systems may be expensive and may also require the patient/user to have to remember another process step when they wish to remove the dressing prior to dressing change. For some homecare products, it is desirable to have a simple automatic way to trigger the switching of the adhesive. In some embodiments of the present systems, a solution to these issues may be achieved by providing a switchable adhesive that can adequately seal the wound site, requires no additional process steps for the user/patient, and can result in the dressing being removed without the risk of patient skin damage or pain.

Disclosed are various embodiments of a light deactivated adhesive drape system configured to be coupled to tissue. In some embodiments, the system comprises: a drape comprising: a photosensitive adhesive layer having at least one release agent disposed within the adhesive layer, wherein the at least one release agent is configured to weaken a bond of the adhesive layer to the tissue upon exposure to at least one of a plurality of light wavelengths, and an optical fiber mesh layer configured as a light pipe; and a blocking layer configured to block the plurality of light wavelengths that activate the at least one release agent.

In some embodiments, the optical fiber mesh layer is disposed over the photosensitive adhesive layer and configured to apply the plurality of light wavelengths across a surface of the photosensitive adhesive layer. In some embodiments, the light pipe is actuated upon exposure of at least a portion of the optical fiber mesh layer to the plurality of light wavelengths. In some embodiments, the plurality of light wavelengths includes wavelengths comprising blue through violet portions of the visible light spectrum. In some embodiments, the plurality of light wavelengths includes wavelengths comprising ultraviolet light. In some embodiments, the blocking layer is disposed over the optical fiber mesh layer. In some embodiments, the optical fiber mesh layer is exposed to the plurality of light wavelengths upon removal of the blocking layer. In some embodiments, the blocking layer includes one or more perforations defining an area of a removable patch. In some embodiments, a portion of the optical fiber mesh layer is exposed to the plurality of light wavelengths upon removal of the removable patch. In some embodiments, the removable patch is a peelable patch configured to be separated from the blocking layer at the one or more perforations and peeled off a surface of the optical fiber mesh layer. In some embodiments, the at least one release agent includes a plurality of photo initiators. In some embodiments, the at least one release agent includes a plurality of free radicals.

In some embodiments, the system further includes at least one reflective material embedded into the blocking layer. In some embodiments, the at least one reflective material includes one or more of silver, titanium dioxide, and zinc oxide. In some embodiments, the at least one reflective material is embedded into an inner surface of the blocking layer facing the optical fiber mesh layer.

In some embodiments, the system further comprises: a control system coupled to the drape, the control system including: a memory configured to store executable instructions that operate the control system; at least one processor configured to execute the executable instructions to operate the control system; and at least one sensor configured to sense a removal state of the drape. In some embodiments, the removal state corresponds to a state where the drape has reached full absorbent capacity. In some embodiments, the control system automatically actuates a light source configured to expose the optical fiber mesh layer to the plurality of light wavelengths upon sensing the removal state of the drape.

In some embodiments, the system further comprises an alarm configured to issue an alert upon sensing the removal state of the drape. In some embodiments, the system further comprises one of a selectable switch or button configured to, upon a selection, actuate a light source configured to expose the optical fiber mesh layer to the plurality of light wavelengths. In some embodiments, the system further comprises a visual indicator configured to issue a visual alert upon sensing the removal state of the drape. In some embodiments, the optical fiber mesh layer is transparent and enabled to allow the plurality of light wavelengths to pass through the optical fiber mesh layer and contact the photosensitive adhesive layer.

In some embodiments, a light deactivated adhesive drape system is configured to be coupled to tissue, the system comprising: a drape comprising: a photosensitive adhesive layer having at least one release agent disposed within the adhesive layer, wherein the at least one release agent is configured to weaken a bond of the adhesive layer to the tissue upon exposure to at least one of a plurality of light wavelengths, and a flexible polymer light pipe; and a blocking layer configured to block the plurality of light wavelengths that activate the at least one release agent. In some embodiments, the light pipe is disposed over the photosensitive adhesive layer and configured to apply the plurality of light wavelengths across a surface of the photosensitive adhesive layer. In some embodiments, the light pipe is one of a pneumatic or fluidic connection tube coupled to a remote therapy device. In some embodiments, the light pipe is silicone.

In some embodiments, a method comprises: coupling a light deactivated adhesive drape system to a patient's tissue; sensing a drape state of the drape; comparing a drape state to a threshold corresponding to a removal state; determining that the drape state reaches the removal state; exposing the photosensitive adhesive layer to the at least one of the plurality of light wavelengths configured to weaken the bond of the adhesive layer; and removing the drape from the tissue. In some embodiments, the method further comprises automatically actuating a light source configured to expose the light pipe to the plurality of light wavelengths upon sensing the removal state of the drape. In some embodiments, the method further comprises actuating an alarm to issue an alert upon sensing the removal state of the drape. In some embodiments, the method further comprises actuating a visual indicator to issue a visual alert upon sensing the removal state of the drape. In some embodiments, the method further comprises selecting one of a selectable switch or button configured to, upon a selection, actuate a light source configured to expose the optical fiber mesh layer to the plurality of light wavelengths. In some embodiments, the method further comprises removing a portion of the blocking layer from the drape system. In some embodiments, the method further comprising removing the entire blocking layer from the drape system.

The foregoing has outlined rather broadly the features and technical advantages of the present disclosure in order that the detailed description that follows may be better understood. Additional features and advantages of the disclosed embodiments will be described hereinafter that form the subject of the claims of the disclosure. It should be appreciated by those skilled in the art that the conception and specific embodiments disclosed may be readily utilized as a basis for modifying or designing other structures for carrying out the same purposes of the present disclosed embodiments. It should also be realized by those skilled in the art that such equivalent constructions do not depart from the spirit and scope of the disclosed embodiments as set forth in the appended claims. The novel features that are believed to be characteristic of the disclosed embodiments, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosed embodiments.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

Any embodiment of any of the disclosed methods, systems, system components, or method steps can consist of or consist essentially of—rather than comprise/include/contain/have—any of the described elements, steps, and/or features. Thus, in any of the claims, the term "consisting of"

or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Figure 1A:
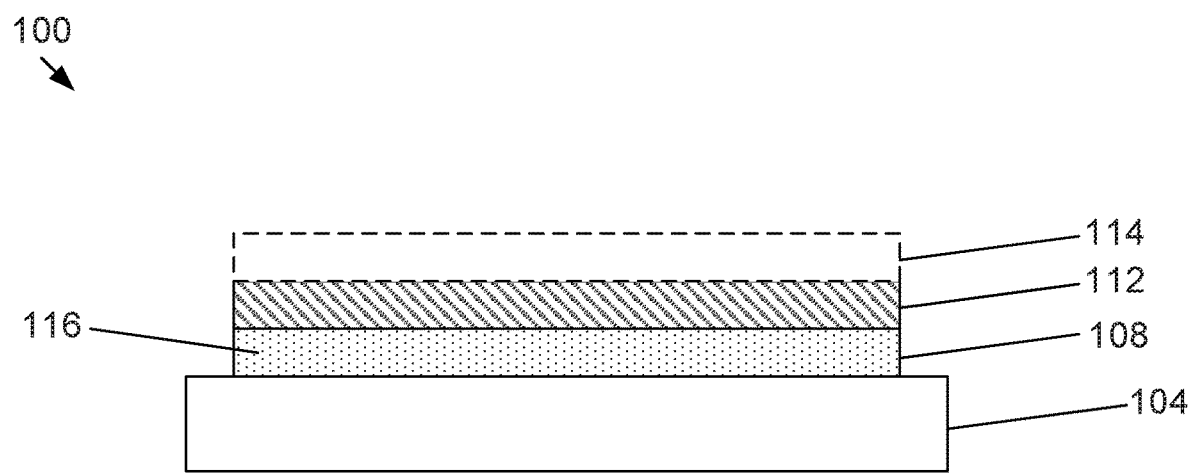
FIGS. 1A-1B are cross-sectional views of a light deactivated adhesive drape system in accordance with an illustrative embodiment of the present disclosure.

In the following detailed description of the preferred embodiments, reference is made to the accompanying drawings that form a part hereof, and in which is shown by way of illustration specific preferred embodiments in which the invention can be practiced. These embodiments are described in sufficient detail to enable those skilled in the art to practice the invention, and it is understood that other embodiments can be utilized and that logical structural, mechanical, electrical, and chemical changes can be made without departing from the spirit or scope of the invention. To avoid detail not necessary to enable those skilled in the art to practice the invention, the description can omit certain information known to those skilled in the art. It is understood that reference to a feature by numeric designation does not necessarily refer only to any particular embodiment depicted in a drawing. The following detailed description is, therefore, not to be taken in a limiting sense, and the scope of the present invention is defined only by the appended claims.

The following definitions are provided to better define the present invention and to guide those of ordinary skill in the art in the practice of the present invention. Unless otherwise noted, terms are to be understood according to conventional usage by those of ordinary skill in the relevant art.

Reduced pressure generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" can be used to describe the pressure applied to the tissue site, the actual pressure applied to the tissue site can be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

As used herein, the term "coupled" includes "indirect coupling" via a separate object. For example, a drape can be coupled to the tissue site if both the drape and the tissue site are coupled to one or more third objects, such as a release agent or a second adhesive layer. The term "coupled" also includes "directly coupled," in which case the two objects touch each other in some way. The term "coupled" also encompasses two or more components that are continuous with one another by virtue of each of the components being formed from the same piece of material. Also, the term "coupled" includes chemical coupling, such as via a chemical bond, and electrostatic coupling.

Various aspects of the present invention comprise a system and method for systems and methods for mitigating premature light deactivation of light deactivated adhesive drapes, a portion of which is shown in each of the FIGS. 1A-8. Various embodiments can facilitate the removal of the drape from the tissue site with less trauma to a patient than conventional drapes while preventing premature deactivation of the adhesive. The tissue site may be skin tissue, wound tissue, bone tissue, or any other type of tissue. Various embodiments of the system and method described herein comprise, or can be used with reduced or negative pressure wound healing technology.

Figure 1B:
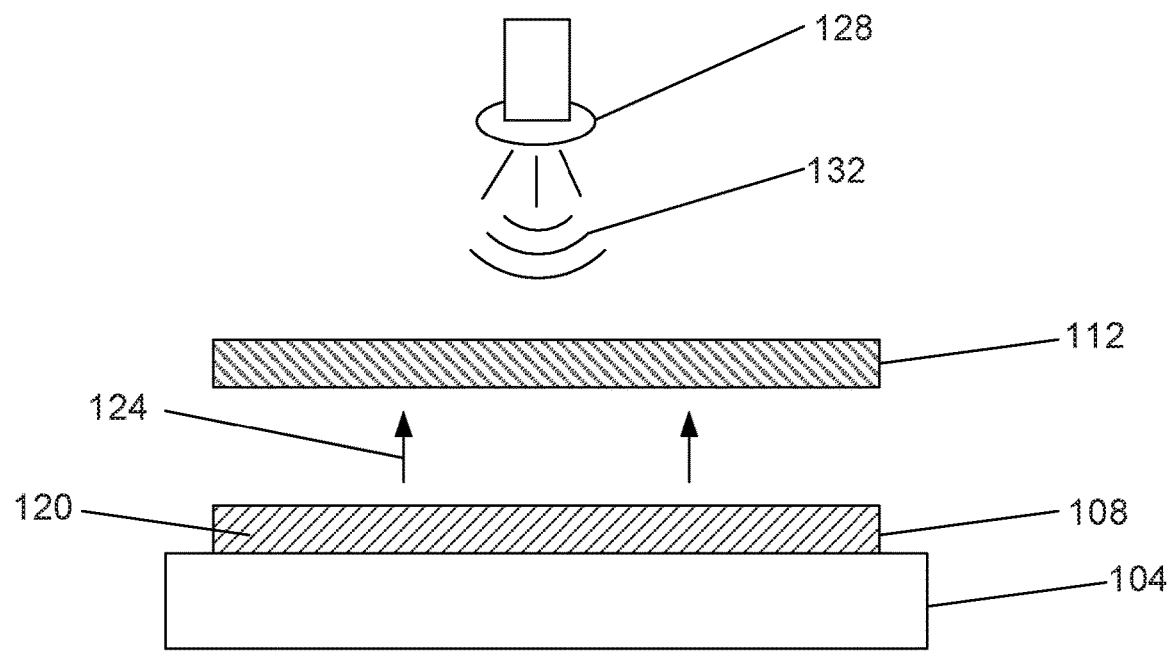

Referring more specifically to FIGS. 1A and 1B, an illustrative embodiment of a light deactivated adhesive drape system 100 disposed onto patient tissue 104 is shown. The system 100 comprises a photosensitive adhesive layer 108 coupled to a flexible film layer 112. In some embodiments, the drape includes both adhesive layer 108 and flexible film layer 112. In the embodiments shown, a drape can be generally understood to be a covering over a tissue 104 that is preferably sterilizable. A drape can comprise a biocompatible thin film material, such as a polymer, a woven or non-woven material, an elastic or non-elastic material, an occlusive or nonocclusive material, and a flexible or inflexible material. A drape can comprise an impermeable, semipermeable, or permeable material. Permeability characteristics can be selected according to desired moisture and gas (e.g., oxygen) transmission. In some embodiments, the drape comprises a material relatively impermeable to moisture and relatively permeable to oxygen. A drape can be coated with a material, for example, to control breathability. A drape can comprise a material which allows or facilitates transmission of external stimuli, such as light, sound, moisture or heat. For example, a drape material can be semi- or substantially transparent to electromagnetic radiation, such as visible, ultraviolet (UV), or infrared light. For example, the drape (e.g., one or more layers thereof) may transmit a substantial or majority portion of a particular type of light. A drape can be composed of one or more layers. In some embodiments, a drape can be a bilayer drape. For example, a bilayer drape can comprise flexible film layer 112 comprising any biocompatible thin film suitable for tissue or wound contact and a second layer 114 comprising a protective material. As another example, three, four, or more drape layers may be used, with combinations of materials selected according to desired function.

In the embodiment shown, the flexible film layer 112 may be a breathable and/or semiporous film such as polyurethane but other suitable materials may be used. The adhesive layer 108 adheres to the tissue 104 thereby coupling the flexible film layer 112 to the tissue 104. The adhesive layer 108 may cover any portion of the flexible film layer 112 and the tissue 104 as may be required. The adhesive layer 108 can comprise any material, in single or multiple layers, capable of adhering to tissue 104. In some embodiments, prior to the application of a drape to a tissue 104, the adhesive layer 108 can also be covered by an adhesive support layer (not shown). The adhesive support layer can provide rigidity to the drape prior to application and can also aid in the actual application of the drape onto tissue 104. The adhesive support layer can be peeled off or otherwise removed to expose adhesive layer 108 before applying the drape to the tissue. The adhesive layer 108 can comprise one or more materials including, but not limited to, polyurethane, acrylic (e.g., cyanoacrylate), hydrogel, silicon or silicone based material, natural rubber, synthetic rubber, styrene block copolymers, polyvinyl ethers, poly(meth)acrylates, polyolefins, hydrocolloid (e.g., a rubber based hydrocolloid), or a combination thereof. In some embodiments, the adhesive layer 108 comprises a polymer or co-polymer. For example, the adhesive layer 108 can comprise a co-polymer of polyurethane and silicone or various acrylic co-polymers.

The adhesive layer 108 may include at least one release agent 116 comprising a release material. In the embodiment shown, adhesive layer 108 has a plurality of release agents 116 (represented by dots). The release agent 116 can physically or chemically affect adhesion characteristics between a drape and a tissue 104. A release agent 116 can comprise a variety of molecular compositions depending on the particular embodiment being implemented, including but not limited to a photopolymer, an oil particle, a gas particle, a solvent, a lipid, and/or one or more microstructures. Release agents 116 can be present in an inert or inactive form in, on, or near an adhesive layer 108. For example, a release agent 116 can be mixed with the adhesive; on the surface of the adhesive with a random or patterned coverage; coupled to the drape with a random or patterned coverage; or contained within a microstructure located in these or other locations. Upon release or activation, release agents 116 can migrate within the adhesive layer 108 or along an interface between an adhesive layer 108 and a tissue 104 to facilitate the removal of a drape affixed thereto. In the embodiment shown, the release agent 116 is configured to transition from an unreleased state (shown in FIG. 1A) to a release state 120 (represented by diagonal lines in FIG. 1B) to weaken a bond of the adhesive layer 108 to the tissue 104 upon exposure to an external stimulus. Various external stimulus can be employed depending on the particular embodiment being implemented. Non-limiting examples of the external stimulus include electromagnetic (e.g., UV, visible, or infrared light), magnetic, sound, pH, pressure (e.g., positive atmospheric pressure, negative atmospheric pressure, shear force, direct force), thermal, moisture, or a substance. The external stimulus can also be a substance, compound, liquid, or gas capable of reacting with a release agent 116 in adhesive layer 108 such that the release agent 116 transitions from an unreleased state to a released state. In the embodiment shown, the external stimulus is one or more of a plurality of light wavelengths. The weakened bond that occurs as a result of the release of release agent 116 allows a user of the light deactivated adhesive drape system 100 to apply an upward force on flexible film layer 112, such as a force indicated by arrow 124, to remove flexible film layer 112 from tissue 104. The weakened bond reduces the stress applied to tissue 104 in the removal of flexible film layer 112 from tissue 104. Thus, a patient feels less pain and discomfort when the flexible film layer 112 is removed. A residue of molecules from adhesive layer 108 might remain on tissue 104 after removal of flexible film layer 112 depending on a variety of factors such as the type of release agent used.

Referring more specifically to FIG. 1A, in the embodiment shown, release agents 116 are inertly dispersed within adhesive layer 108 and can be located anywhere within adhesive layer 108, as well as any of the outer surfaces of adhesive layer 108, such as an interface between adhesive layer 108 and flexible film layer 112. In some embodiments, release agents 116 can be bonded or coupled directly to flexible film layer 112, and a separate film layer (not shown in FIG. 1A), can separate release agents 116 from adhesive layer 108. In these embodiments, the presence of an external stimulus can weaken, break-down, or increase the permeability of the separate film layer such that release agents 116 are allowed to migrate into adhesive layer 108 to facilitate the removal of flexible film layer 112 from tissue site 105. As shown in FIG. 1B, release agents 116 may be released in the presence of external stimulus such that release agents 116 are allowed to migrate within adhesive layer 108 and the interface between adhesive layer 108 and tissue 104. In the embodiment shown, a UV light source 128 exposes flexible film layer 112 and adhesive 108 to a plurality of light wavelengths 132. In some embodiments, exposure to the plurality of light wavelengths 132 can cause microstructures containing release agents 116 to rupture or tear, thereby releasing release agents 116 from the interior of the microstructures. These released release agents 116 can then be interspersed into adhesive layer 108 and the interface between adhesive layer 108 and tissue 104, thereby weakening the bond between flexible film layer 112 and tissue 104 and facilitating the removal of flexible film layer 112 from tissue 104. As the plurality of light wavelengths 132 reach adhesive 108, release agents 116 may transition from an unreleased state (as shown in FIG. 1A) to a released state 120 (as shown in FIG. 1B) as they are exposed to the plurality of light wavelengths 132. In the embodiment shown, the plurality of light wavelengths 132 are UV wavelengths. In some embodiments, the UV wavelengths may be within a range of 280 nm-380 nm, although it may be preferable to have the UV wavelengths be UVA wavelengths within a range of 315 nm-380 nm.

Figure 2A:
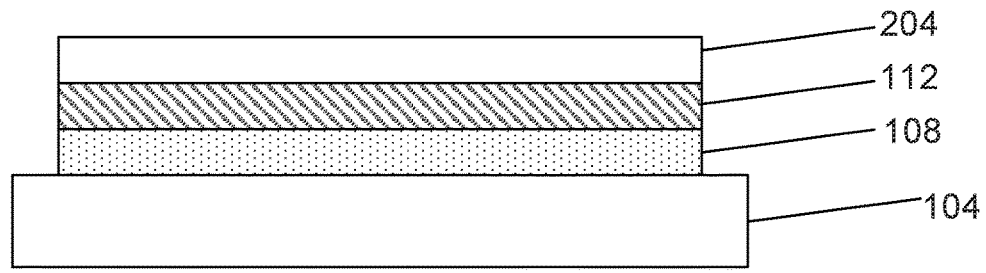
FIGS. 2A-2C are cross-sectional views of a light deactivated adhesive drape system in accordance with another illustrative embodiment of the present disclosure.
Figure 2B:
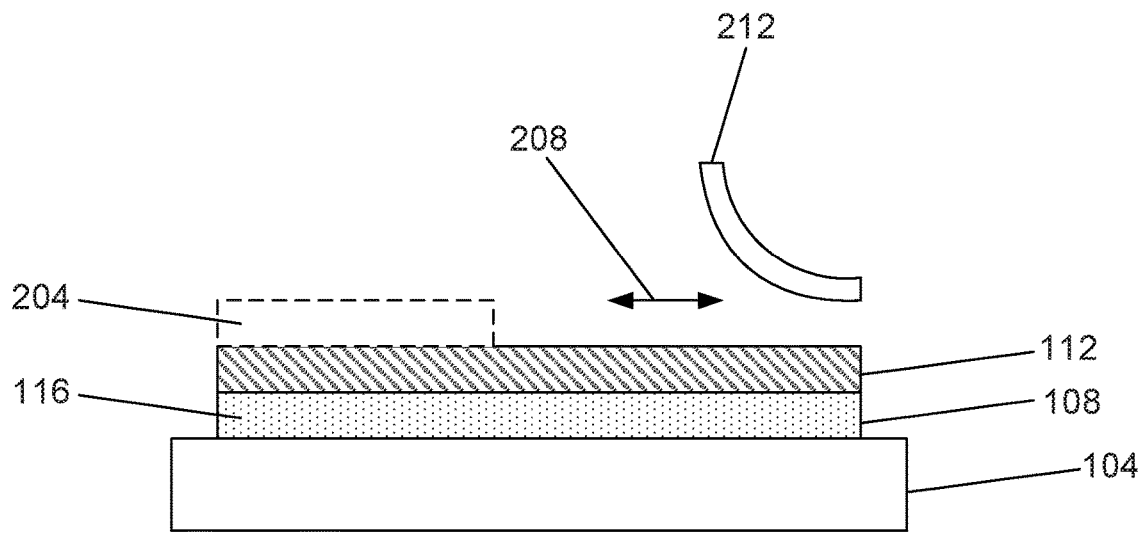
Figure 2C:
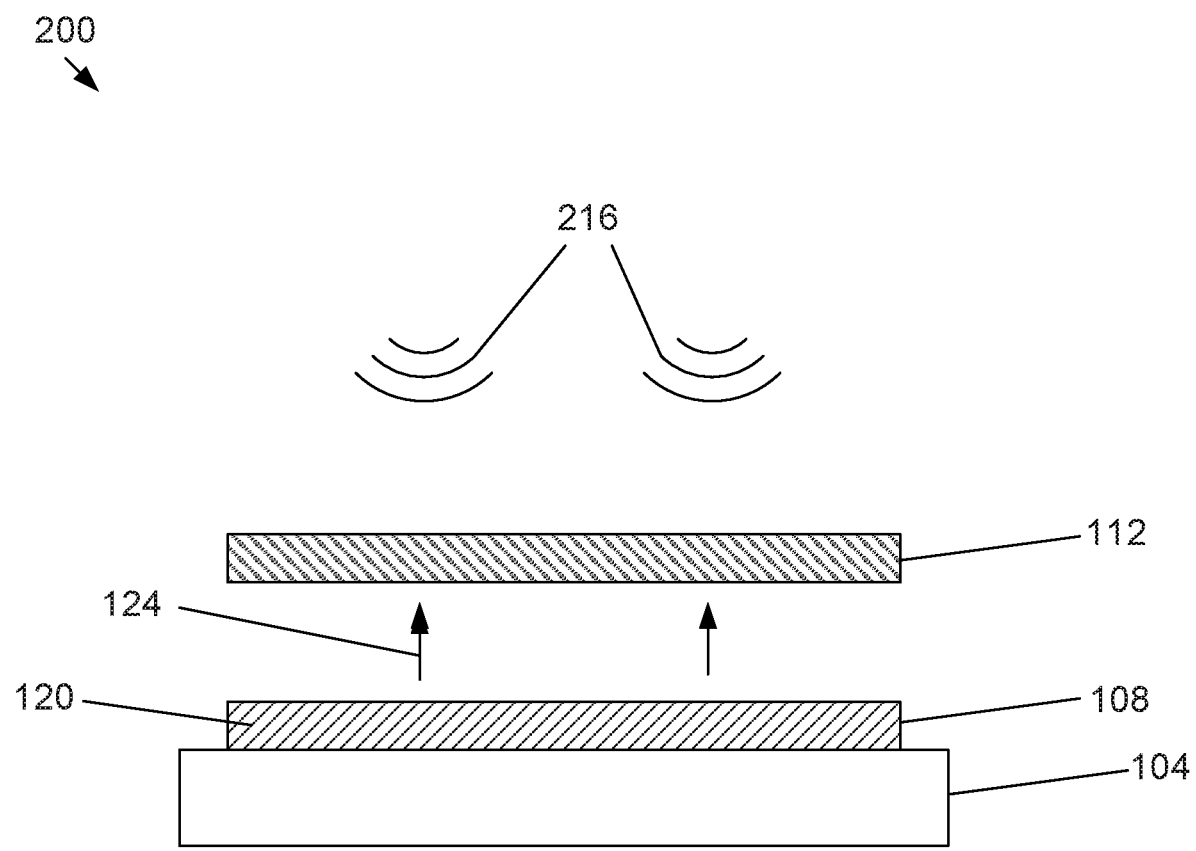

Referring now to FIGS. 2A-2C, another illustrative embodiment of a light deactivated adhesive drape system 200 disposed onto patient tissue 104 is shown. In this embodiment, light deactivated adhesive drape system 200 is configured to release adhesive layer 108 upon exposure to ambient, visible light instead of UV light. Although having adhesive layer 108 release upon exposure to visible light is advantageous in that it doesn't require a specific UV light source and enables release to occur in any environment having ambient light, it also can increase a likelihood that the adhesive layer 108 will prematurely deactivate. In order to prevent premature deactivation, the adhesive layer 108 may be constructed with release agents 116 that only release upon exposure to certain wavelengths of visible light. For example, in the embodiment shown, release agents 116 will only transition to an unreleased state 120 when exposed to visible light wavelengths in the blue and violet portions of the visible light spectrum. In the embodiment shown, a blocking layer 204 is disposed over flexible film layer 112 of the drape. In this embodiment, blocking layer 204 is configured to block the visible light wavelengths that release the adhesive layer 108.

In the embodiment shown in FIG. 2B, blocking layer 204 is configured to be removable. This enables the adhesive layer 108 to be deactivated at a time a user desires to remove the drape from tissue 104. In the embodiments shown, blocking layer 204 is a removable, peelable layer disposed directly onto the drape or the adhesive layer 108. In some embodiments, blocking layer 204 may comprise a layer that covers the entire outer surface of the drape or may only cover a portion of the outer surface of the drape. After the drape is been applied to tissue 104, the blocking layer 204 may be removed by applying a force (e.g., in one or more directions represented by arrows 208) to peel off at least one removable portion 212 of blocking layer 204. As shown in FIG. 2C, once blocking layer 204 has been removed, the adhesive layer 108 can be exposed to deactivation wavelengths (e.g., ambient light 216) that comprises light wavelengths configured to deactivate adhesive layer 108. Upon exposure to ambient light 216, release agents 116 can transition from an unreleased state to a released state 120. The drape including flexible film layer 112 can then be removed from tissue 104. If any residue of adhesive layer 108 remains on tissue 104 after removal of the drape, it may be removed.

Figure 3:
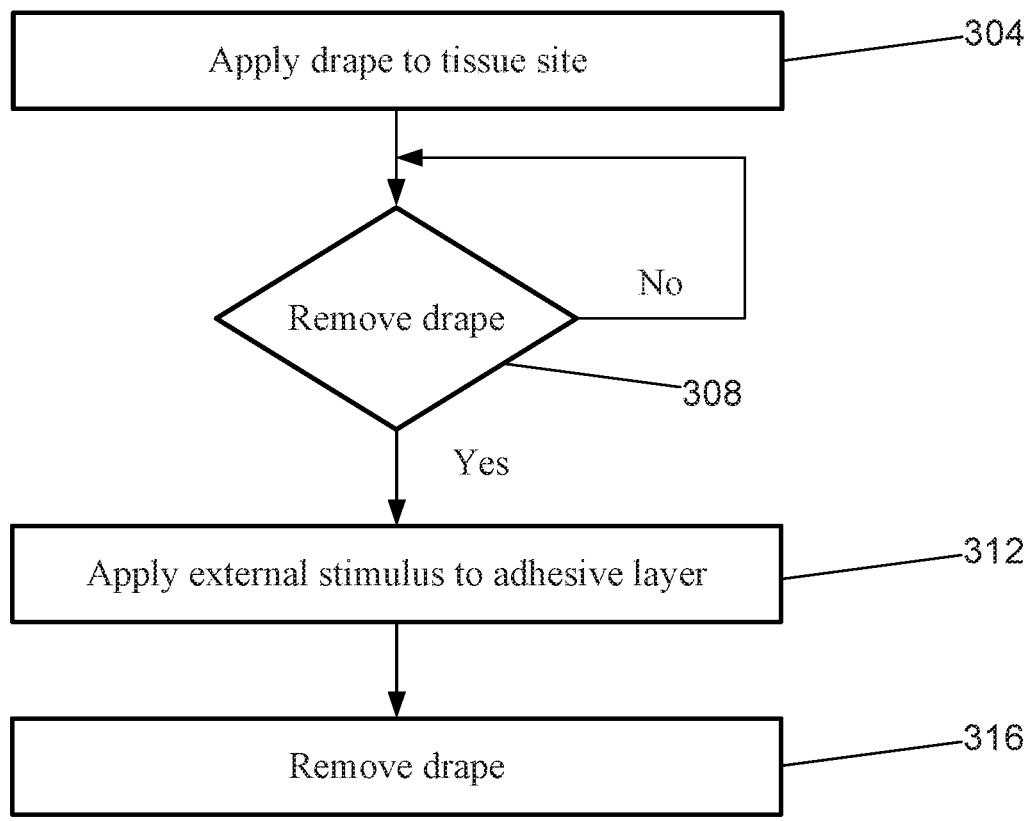
FIG. 3 is a flowchart illustrating a process for using a light deactivated adhesive drape system in accordance with an illustrative embodiment of the present disclosure.

FIG. 3 depicts a flowchart illustrating a general process 300 for facilitating removal of a light deactivated adhesive drape system (e.g. 100, 200) from a tissue 104 in accordance with an illustrative embodiment of the disclosure. The process illustrated in FIG. 3 can be implemented by a user of a reduced or negative pressure treatment system. The process begins by applying a drape to a tissue 104 (step 304). In this step, adhesive layer 108 can bind to the tissue 104. Also in this step, reduced or negative pressure can be applied to the tissue 104 using a reduced or negative pressure treatment system. The process determines whether to remove the drape from the tissue 104 (step 308). If the process determines not to remove the drape from the tissue 104, the process returns to step 308. If the process determines to remove the drape from the tissue 104, the process applies an external stimulus to the drape, including the adhesive layer 108 coupled to the drape (step 312). In this step, a release agent 116 can be released in accordance with any of the illustrative embodiments described above to facilitate the removal of the drape from the tissue 104. The process then removes the drape from the tissue 104 (step 316).

Figure 4:
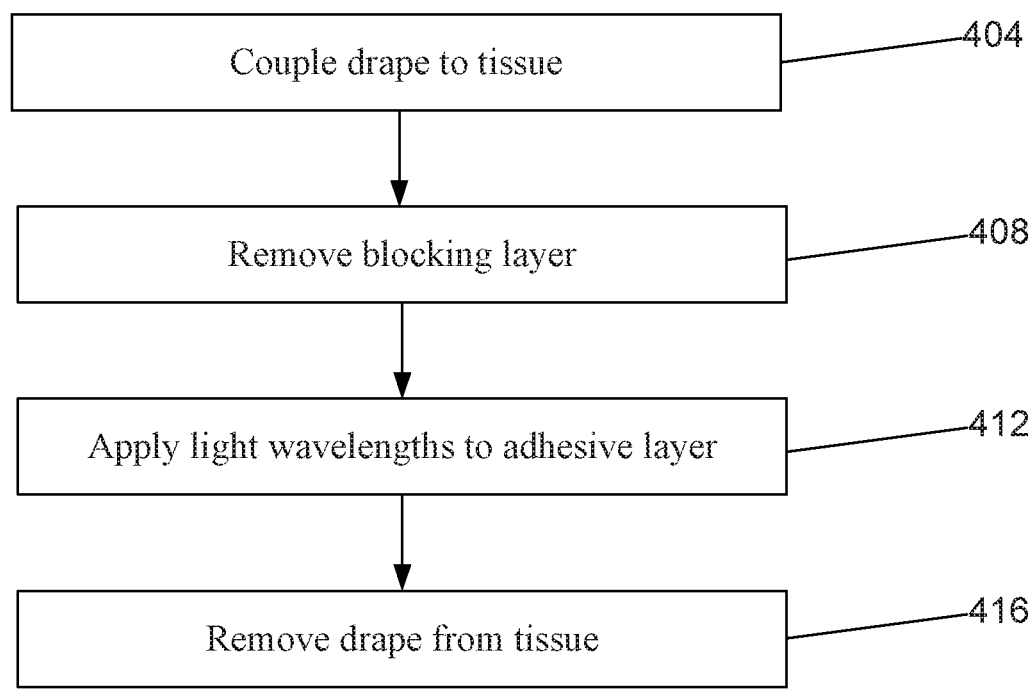
FIG. 4 is a flowchart illustrating a process for using a light deactivated adhesive drape system in accordance with another illustrative embodiment of the present disclosure.

FIG. 4 depicts a flowchart illustrating process 400 for facilitating removal of a light deactivated adhesive drape system (e.g. 100, 200) from a tissue 104 in accordance with an illustrative embodiment of the disclosure. Referring to FIG. 4, process 400 begins by coupling a drape to a tissue (step 404). In this embodiment, the drape may have a removable blocking layer that is configured to be removed entirely or have a portion removed. Process 400 continues by, when the drape is desired to be removed, the removable blocking layer or a portion of the removable blocking layer is peeled off or otherwise removed from the drape (step 408). Process 400 continues by applying certain deactivating light wavelengths to the photosensitive adhesive layer to deactivate the adhesive (step 412). The process then enables a removal of the drape from the tissue (step 416).

Figures 5A, 5B:
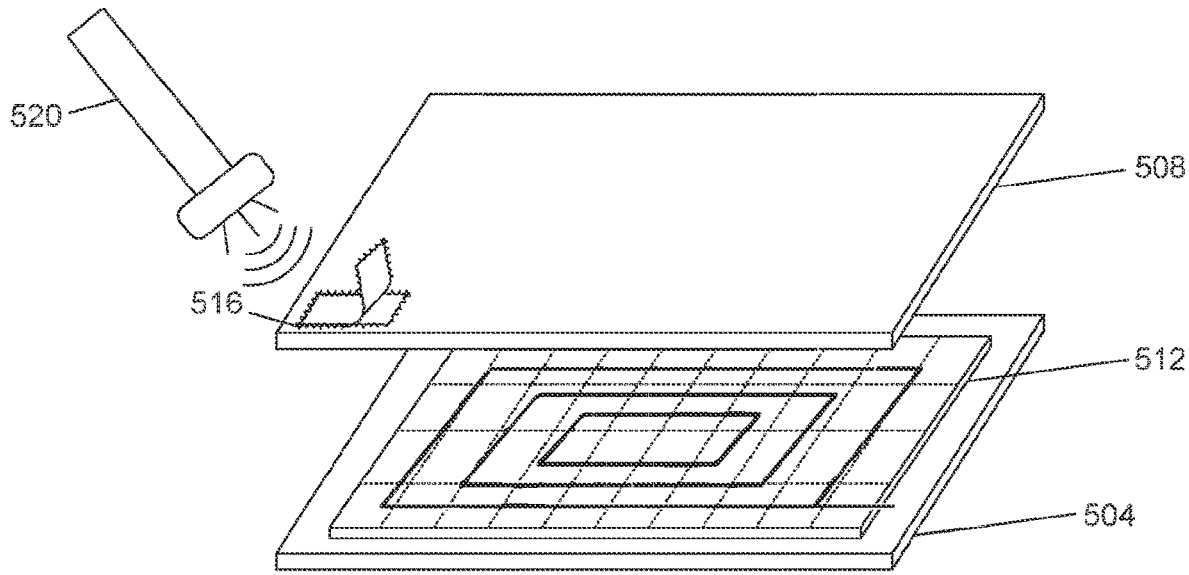
FIGS. 5A-5B are perspective views of a light deactivated adhesive drape system in accordance with another illustrative embodiment of the present disclosure.

Referring now to FIGS. 5A-5B, another illustrative embodiment of a light deactivated adhesive drape system 500 disposed onto patient tissue 104 is shown. This embodiment includes a high-bond strength adhesive dressing with trauma-free removal that utilizes a light sensitive skin adhesive layer 504 and is protected from light deactivation (UV or visible light) by a light blocking/opaque film 508. Light deactivated adhesive drape system 500 further includes a light pipe element 512. Light pipe element 512 is configured to transmit and distribute the deactivating light wavelengths across a surface (e.g., the adhesion surface) of light sensitive skin adhesive layer 504 such that the light wavelengths deactivate the light sensitive adhesive more rapidly and effectively. In the embodiment shown, light pipe element 512 corresponds to or is incorporated into its own discrete layer. Light pipe element 512 may include one or more diffusers (diffuser elements) which diffuse the light.

In the embodiment shown, light pipe element 512 is comprised of a mesh of flexible, plastic/polymer optical fiber mono-filaments that are bonded to the light sensitive skin adhesive layer 504. Responsive to receiving light, the light pipe element 512 (e.g., mono-filaments thereof) may internally reflect the light, such as reflect the light within an interior cavity thereof or within the polymer material itself by internal reflections from an exterior surface thereof. In some embodiments, the mesh includes transparent portions that enable light wavelengths to pass through the mesh and contact the light sensitive skin adhesive layer 504. In the embodiment shown, the light blocking film 508 is bound onto the optical fiber mono-filaments of light pipe element 512 to protect the light sensitive adhesive from premature deactivation. In the embodiment shown, a small section of the light blocking/opaque film 512 is perforated or otherwise separable from the light blocking/opaque film 512 to constitute a removable (e.g., peelable) patch 516. As shown in FIG. 5B, when the dressing is ready for removal, the perforated, peelable patch 516 is removed/peeled off a surface of the mesh layer to remove a portion of the light blocking/opaque film 512 and enable the mesh of optical fiber mono-filaments to be exposed to deactivating light wavelengths from a natural or artificial light source 520. In this way, a light-pipe effect will be created and the mesh of optical fiber mono-filaments will distribute the deactivating light wavelengths effectively throughout the dressing and across the entire surface of the light sensitive adhesive layer 504. The deactivating light wavelengths can be efficiently distributed to the entire light sensitive adhesive layer 504 while only directly exposing a small portion of the light sensitive adhesive layer 504 to the deactivating light wavelengths. This may reduce the deactivation time of the light sensitive adhesive layer 504 and only require a small section of the dressing to be exposed. As a result, the time required for a patient to lie in an uncomfortable position and/or the area of the dressing required to be exposed to light can be reduced.

Figure 6A:
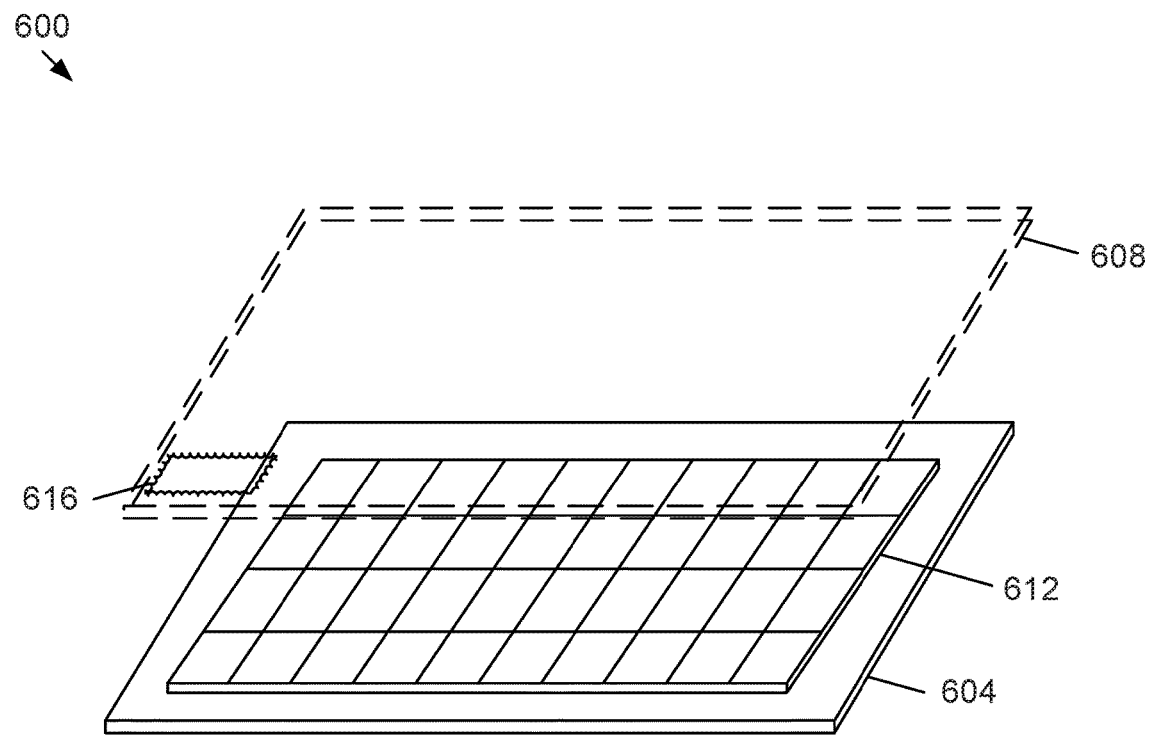
FIGS. 6A-6B are perspective views of a light deactivated adhesive drape system in accordance with another illustrative embodiment of the present disclosure.
Figure 6B:
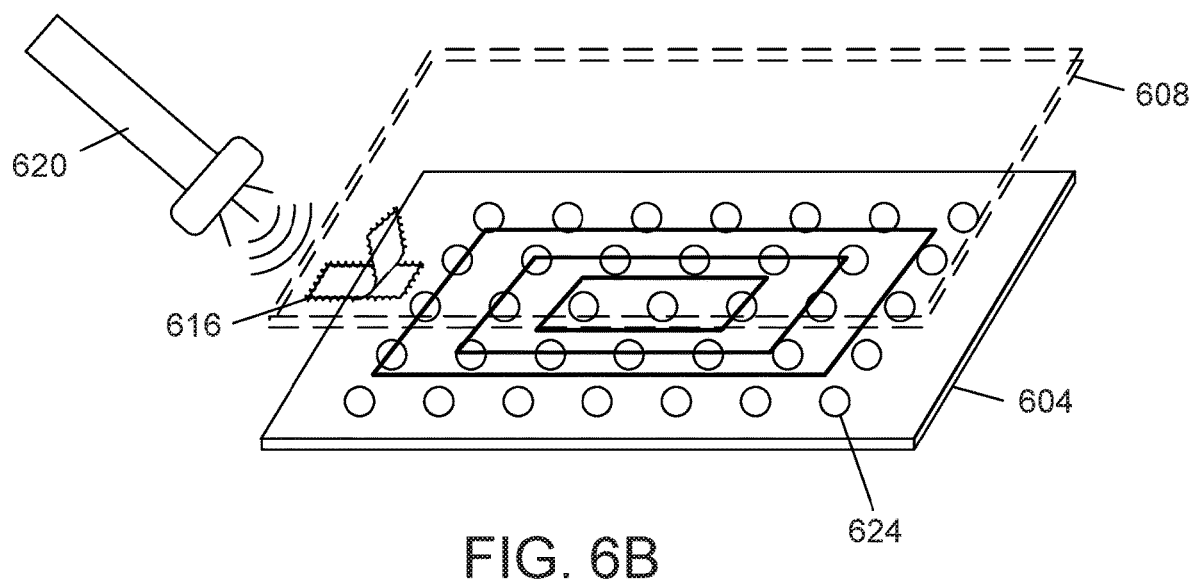

Referring now to FIGS. 6A-6B, another illustrative embodiment of a light deactivated adhesive drape system 600 disposed onto patient tissue 104 is shown. Similar to the embodiment shown in FIGS. 5A-5B, this embodiment also includes a high-bond strength adhesive dressing having a light sensitive skin adhesive layer 604 that is protected from light deactivation (UV or visible light) by a light blocking/opaque film 608 (illustrated as transparent in FIGS. 6A-6B to better show other components/layers). In the embodiment shown, a light pipe element 612 is provided that helps to transmit and distribute the deactivating light wavelengths across the adhesion surface of light sensitive skin adhesive layer 604 such that the light wavelengths deactivate the light sensitive adhesive more rapidly and effectively.

In the embodiment shown in FIGS. 6A-6B, free-radical migration is used to trigger adhesive deactivation light sensitive skin adhesive layer 604. In this embodiment, when the dressing is ready to be removed, peelable patch 616 is removed/peeled off to remove a portion of the light blocking/opaque film 612 and enable the mesh of optical fiber mono-filaments to be exposed to deactivating light wavelengths from a natural or artificial light source 620. When the light sensitive skin adhesive layer 604 is exposed to deactivating light wavelengths, the release/migration of free radicals 624 from photo initiators in the light sensitive skin adhesive layer 604 may deactivate larger areas of the adhesive more quickly.

In the embodiments shown, the light pipe effect shown in FIGS. 5A-5B or the movement of free radicals shown in FIGS. 6A-6B may be further enhanced by incorporating one or more additional reflective materials into the light blocking/opaque film 512, 612. These materials can be reflective materials (e.g., materials reflective to light that would otherwise activate the adhesive, such as silver, titanium dioxide, zinc oxide particles) that can be embedded onto an inside layer or into an inner surface of the light blocking/opaque film 512, 612 facing the light sensitive skin adhesive layer 504, 604. By using the embodiments shown, an adhesive deactivation process can be carried out more quickly by enabling more effective light transmission across the adhesion surface of the adhesive layer and, thereby, enabling trauma free removal of larger dressing areas. This can minimize the need for moving patients or having patients remain in a particular position for a lengthy amount of time in order to deactivate the adhesive on the dressing. This may increase patient comfort, reduce patient trauma/injury, and alleviate load lifting concerns for care providers.

Figure 7A:
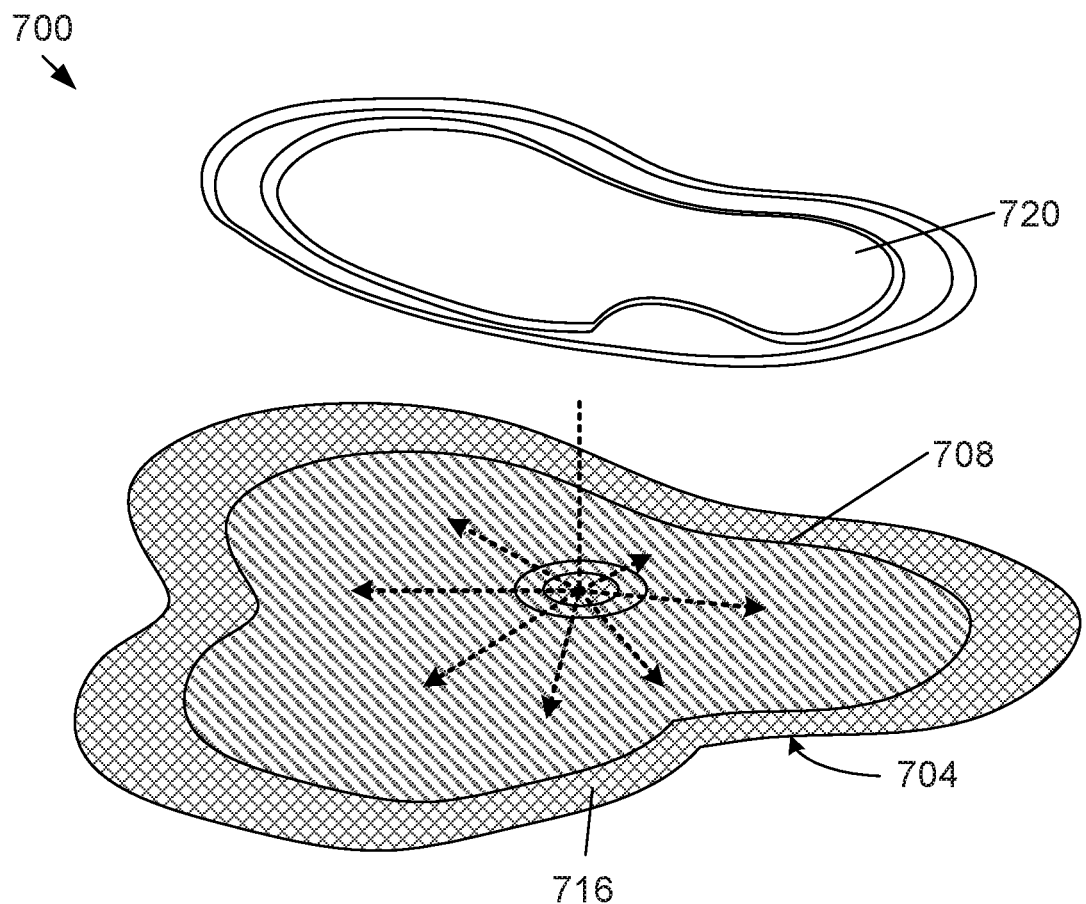
FIG. 7A is a perspective view of a light deactivated adhesive drape system in accordance with another illustrative embodiment of the present disclosure.
Figure 7B:
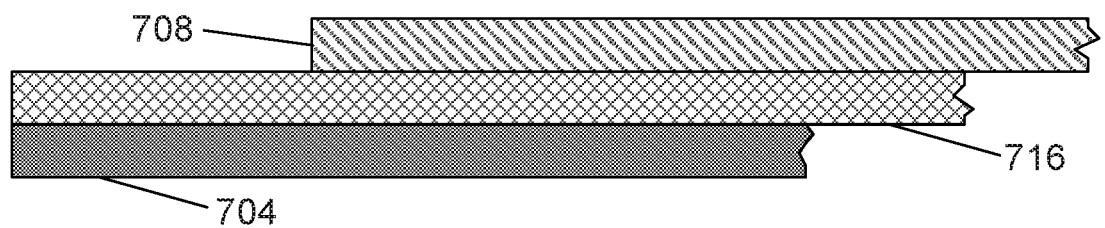
FIGS. 7B-7C are cross-sectional views of the light deactivated adhesive drape system of FIG. 7A.
Figures 7C, 7D:
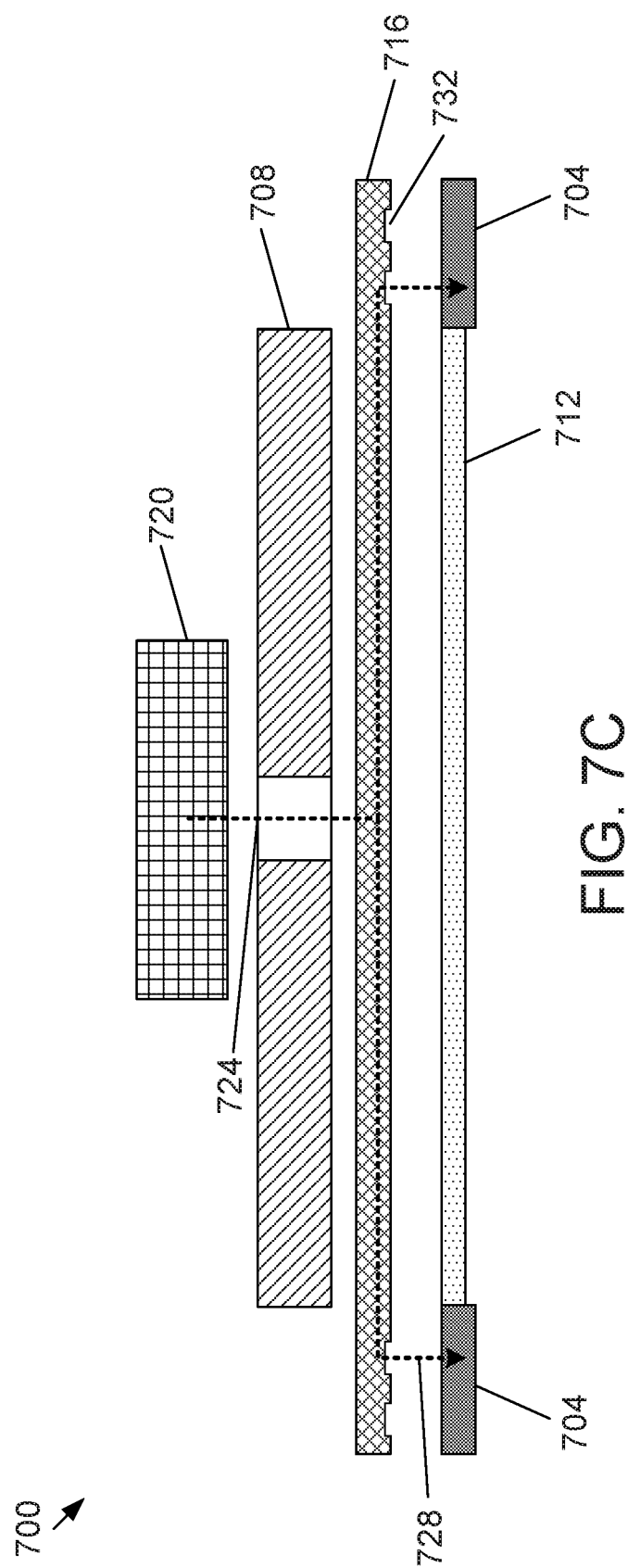
FIG. 7D is a block diagram of an example of a control layer of FIG. 7A.

Referring now to FIGS. 7A-7C, another illustrative embodiment of a light deactivated adhesive drape system 700 disposed onto patient tissue 104 is shown. In the embodiment shown, a light switchable adhesive configured to deactivate upon exposure to certain light wavelengths (e.g., UV or visible light) is placed on the underside of a powered or tethered dressing assembly. In the embodiment shown, the light switchable adhesive is positioned in a layer 704 under one or more edges of an absorbent dressing stack 708 such that a thick sealing light switchable adhesive provides a peripheral seal around the wound. In the embodiment shown, a standard (e.g., acrylic) adhesive 712 can be disposed under the surface of the absorbent dressing stack 708 to provide some measure of adhesion after light switchable adhesive layer 704 has been deactivated. In the embodiment shown, standard adhesive 712 can be perforated (e.g., include one or more perforations 732) or otherwise porous/breathable to allow for fluid communication between the wound and the absorbent dressing stack 708 (e.g., via one or more of 704 or 716).

In other embodiments, light switchable adhesive layer 704 can be positioned under the entire surface of the absorbent dressing stack 708. In some embodiments, the light switchable adhesive is a UV releasable adhesive which requires a light source that emits wavelengths of between 400 and 500 nm for 20 seconds to deactivate the adhesive to a ⅔ reduction in bond strength. Other suitable wavelengths and exposure times may be used; however, each light switchable adhesive requires some exposure to certain light wavelengths for a certain period of time to trigger a release/deactivation of the adhesive.

In the embodiment shown, a flexible film layer 716 (e.g., polyurethane) is disposed over the light switchable adhesive layer 704. In some embodiments, the flexible film layer 716 is transparent. In other embodiments, the flexible film layer is surface treated such that light can be diffused over the entire area of the light switchable adhesive layer 704. In the embodiment shown, a light-pipe element is disposed within or over the flexible film layer 716. In the embodiment shown, this light-pipe element is constructed such that light contacting the light-pipe element is refracted over the total area of the dressing and reflected down through the peripheral areas of the drape where the light switchable adhesive layer 704 is located. In some embodiments, the light-pipe element may be comprised of a flexible and compressible polymer such as a silicone which can be shaped so that it can manifold the light in such a way as to provide a degree of protection to sensitive areas of tissue or a degree of offloading. In the embodiment shown, flexible film layer 716 can be perforated, illustrated as representative perforations 732. In other embodiments, the flexible film layer 716 may be porous/breathable to allow for light and/or fluid communication between the flexible film layer 716 and the light switchable adhesive layer 704.

In the embodiment shown, a control layer 720 (e.g., control device or control system) including an on-board control module and one or more artificial light sources that are controlled by the control module may be positioned as required around the light-pipe element such that a sufficient intensity of light deactivating wavelengths is transmitted over the surface of the light switchable adhesive layer 704. In the embodiment shown, the control module includes at least one processor, at least one memory, and at least one program instruction executable by the at least one processor to perform the various process steps disclosed herein. In the embodiment shown, it is possible to use an adhesive that has double the initial bond strength compared to traditional drapes to improve the seal of the drape to the tissue. This is possible because, after deactivation, the adhesive strength will drop to less than half the release strength of a traditional adhesive.

In the embodiment shown, absorbent stack layer 708 may have one or more apertures 724 (e.g., perforations or through holes as illustrated in FIG. 7C) enabling deactivating light wavelengths emitted from the one or more light sources of control layer 720 to reach the light-pipe element of flexible film layer 716. Similar to the embodiments shown in FIGS. 5A-6B discussed above, only a small portion of the entire light-pipe element needs to be exposed to the deactivating light wavelengths. Once the deactivating light wavelengths contact the light-pipe element of flexible film layer 716 (such as through aperture(s) 724), the light-pipe element distributes the light wavelengths throughout the flexible film layer 716 so that they reach the light switchable adhesive layer 704 (as shown by arrows 728 and through perforations 732 in the example of FIG. 7C).

In some embodiments using a remote or "tethered" drape system, a pneumatic/fluidic connection tube from a remote therapy device can act as the light pipe and deliver the deactivation wavelengths to the dressing to enable the adhesive to be deactivated. In these embodiments, the internal structure of the dressing would be slightly different from the embodiments shown but the principle of light distribution within the dressing via a light-pipe effect is the same. From a system perspective, a user can place the dressing as they would any other dressing. Unlike many other dressing technologies, this can be done in a single step operation where the release liners are removed and the dressing is applied to tissue. The user can then activate the control module on the dressing by which, through a variety of possible pump technologies (e.g., disk-pump, diaphragm pump, electro-osmotic element, etc.), negative pressure is generated.

In some embodiments, the light distribution flexible film layer 716 above the adhesive can be transparent to ambient light. In the event of an on-board failure of the control module and/or the light sources, the adhesive may still be deactivated either by a longer duration exposure to ambient, white light or by using a separate UV light source. In other embodiments, ultrasonic frequencies may be used to trigger the release of the adhesive. In these embodiments, a suitable waveguide can be provided to replace the light-pipe that can transmit surface acoustic waves to trigger the release of micro-encapsulated release agents within the adhesive to enable the drape to be easily removed. In some embodiments, certain tuned shapes and thicknesses of the flexible film layer 716 (e.g., polyurethane layer) can act as an appropriate waveguide.

A drape can be determined to be in one of multiple drape states during the treatment course based on its saturation state. For example, a newly applied drape will have a higher absorbent state than a drape that has been on the patient tissue for a long period of time. Usually, there are two main scenarios where the dressing is desired to be removed. One main scenario is when the dressing is full or has reached a certain absorbency threshold that corresponds to a state where the dressing should be replaced. In this case, the control system senses a drape state of the drape, compares the drape state to a threshold corresponding to a drape removal state to determine that the drape should be removed, terminates the therapy, and instructs the user to remove the dressing. In this scenario, the control system may first issue an audible alert to the user to inform the user that the dressing is full and then self-actuate or automatically actuate one or more light sources. These light sources emit deactivating light wavelengths that can both illuminate the dressing (thus providing the user with a visual indicator that the dressing is in the deactivation process) and deactivate the light sensitive adhesive. There may be other scenarios/reasons that the control system may determine that the dressing should be removed and automatically activate the light sources. For example, the control system may detect that the dressing should be removed because at least one sensor has detected that the dressing has reached a full absorbent capacity. The control system may then automatically actuate a light source to initiate a deactivation process. However, each of these scenarios result in the user being notified of the scenario and that a deactivation process will automatically commence. In this way, the control system provides a visible and/or audible indicator to the user that the dressing will be released. This embodiment can also be beneficial in that is fully automated and does not require user engagement in the process of deactivating the switchable adhesive.

The other main scenario is when the user elects to terminate therapy and remove the dressing. In some embodiments, a deactivation button or selectable switch may be provided that is coupled to the control system. If the user elects to remove the dressing, the user actuates the selectable button or switch (e.g., press the button, flip the switch/selector button) to trigger the light sources to illuminate and deactivate the light sensitive adhesive.

FIG. 7D illustrates a block diagram of an example of a control layer 720A, such as an example of control layer 720 of FIG. 7A. As illustrated in the example in FIG. 7D, control layer 720A includes a processor 736 and a memory 740. In some implementations, the control layer 720 may further include one or more of a light source 744, a sensor 748, alarm 752, one or more selectable buttons 756, or a visual indicator 760. During operation, the processor 736, executing instructions stored in the memory 740, may activate the light source 744, such as responsive to an input received via a particular selectable button of the one or more selectable buttons 756. The processor 736 may receive sensor data from sensor 748, process the sensor data according to data stored in the memory 740, and generate an indication. The indication may delivered/output via the alarm 752, the visual indicator 760 or both, and may indicate that the light switchable adhesive has been deactivated. Additionally, or alternatively, the sensor 748 may be configured to determine a removal state of the drape, and in some such implementations, the light source 744 is activated responsive to a determination that a removal state of the drape has been detected.

Additionally, features of the drape systems 100, 200, 500, 600, and 700 may be mixed and matched to generate embodiments consistent with the exemplary example embodiments illustrated in the above described figures. For example, a drape of one system may be used with another system. As another example, a feature of a drape of a first drape system may be added to a drape of a second drape system.

Figure 8:
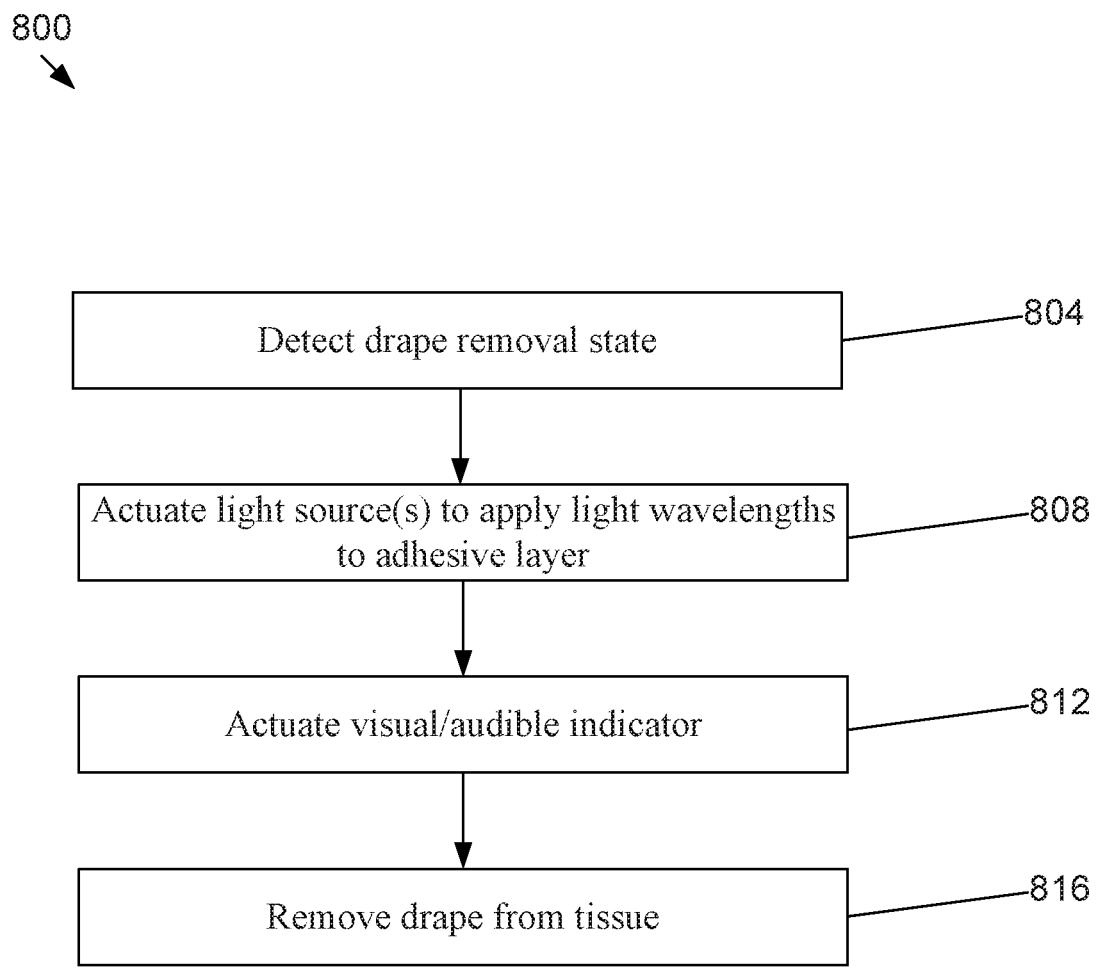
FIG. 8 is a flowchart illustrating a process for using a light deactivated adhesive drape system in accordance with another illustrative embodiment of the present disclosure.

FIG. 8 depicts a flowchart illustrating an automated process 800 for facilitating removal of a light deactivated adhesive drape system (e.g. 100, 200, 500, 600, or 700) from a tissue 104 in accordance with an illustrative embodiment of the disclosure. In this embodiment, process 800 is executed by a drape control system that includes at least one processor, at least one memory, and at least one program instruction stored in the memory and executable by the at least one processor to perform the steps of process 800. Referring to FIG. 8, process 800 begins by detecting a drape removal state via at least one sensor (step 804). To illustrate, the sensor may generate sensor data on a saturation level of the drape, and a processor may compare the saturation level to a threshold saturation level to determine a removal state of the drape. As discussed above, a drape removal state may correspond to any scenario where the drape should be removed, such as when the drape is saturated (e.g., fully saturated or reached full absorbent capacity) and needs to be replaced or when the drape is saturated to a designed or operating capacity, such as 80 percent saturated. Saturation of the drape may be determined by the maximum amount of 0.9 weight percent (wt %) saline solution (e.g., sodium chloride in water) that a drape can retain under free swelling conditions at room temperature and humidity.

Process 800 continues by, when the drape removal state is detected by at least one sensor, automatically actuating at least one light source to emit deactivating light wavelengths onto at least a portion of the light-pipe element to deactivate the adhesive (step 808). Process 800 continues by actuating one or more of an audible/visual indicator (e.g., alarm, flashing light, etc.) to issue an alert to notify the user that a deactivation process has been actuated (step 812). The process then enables a removal of the drape from the tissue (step 816).

The flowcharts and block diagrams in the different depicted embodiments illustrate the architecture, functionality, and operation of some possible implementations of the apparatus and methods. Such flowcharts and block diagrams include FIGS. 3, 4, and 8. Such flowcharts and block diagrams may be useable with the drapes of FIGS. 1A, 1B, 2A-2C, 5A, 5B, 6A, 6B, and 7A-7D. In some alternative implementations, the function or functions noted in the block can occur out of the order noted in the figures. For example, in some cases, two blocks shown in succession can be executed substantially concurrently, or the blocks can sometimes be executed in the reverse order, depending upon the functionality involved. Additionally or alternatively, in some other implementations, a function of one or more blocks may be omitted. Similarly, a function of a block of another method or device described herein can be added.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A light deactivated adhesive drape system configured to be coupled to tissue, the system comprising:
   a drape comprising:
      a photosensitive adhesive layer having at least one release agent, wherein the at least one release agent is configured to weaken a bond of the adhesive layer to the tissue upon exposure to at least one of a plurality of light wavelengths, and
      an optical fiber mesh layer configured as a light pipe; and
   a blocking layer configured to block the plurality of light wavelengths that activate the at least one release agent.

2. The system of claim 1, wherein the optical fiber mesh layer is disposed over the photosensitive adhesive layer and configured to apply the plurality of light wavelengths to a surface of the photosensitive adhesive layer.

3. The system of claim 2, wherein the optical fiber mesh layer is configured to function as a light pipe to transport the plurality of light wavelengths to the photosensitive adhesive layer upon exposure of at least a portion of the optical fiber mesh layer to the plurality of light wavelengths.

4. The system of claim 3, wherein the plurality of light wavelengths includes wavelengths comprising blue through violet portions of the visible light spectrum.

5. The system of claim 1, wherein the plurality of light wavelengths includes wavelengths comprising ultraviolet light.

6. The system of claim 5, wherein the optical fiber mesh layer is positioned between the blocking layer and the photosensitive adhesive layer.

7. The system of claim 1, wherein the blocking layer includes one or more perforations defining an area of a removable patch.

8. The system of claim 7, wherein a portion of the optical fiber mesh layer is configured to be exposed to the plurality of light wavelengths upon removal of the removable patch.

9. The system of claim 8, wherein the removable patch is a peelable patch configured to be separated from the blocking layer at the one or more perforations and peeled off a surface of the optical fiber mesh layer.

10. The system of claim 1, wherein the at least one release agent includes a plurality of photo initiators.

11. The system of claim 10, wherein the at least one release agent includes a plurality of free radicals.

12. The system of claim 1, further including at least one reflective material embedded into the blocking layer, the reflective material configured to reflect the light.

13. The system of claim 12, wherein the at least one reflective material includes one or more of silver, titanium dioxide, and zinc oxide.

14. The system of claim 13, wherein the at least one reflective material is embedded into an inner surface of the blocking layer facing the optical fiber mesh layer.

15. The system of claim 1, further comprising: a control system coupled to the drape, the control system including:
   a memory configured to store executable instructions that operate the control system;
   at least one processor configured to execute the executable instructions to operate the control system; and
   at least one sensor configured to sense a saturation level of the drape.

16. The system of claim 15, wherein the at least one processor is configured to compare the sensed saturation level of the drape to a threshold saturation level to determine if the drape has reached a removal state.

17. The system of claim 16, wherein the control system is further configured to automatically actuate a light source configured to expose the optical fiber mesh layer to the plurality of light wavelengths upon sensing the removal state of the drape.

18. A light deactivated adhesive drape system configured to be coupled to tissue, the system comprising:
   a drape comprising:
      a photosensitive adhesive layer having at least one release agent disposed within the adhesive layer, wherein the at least one release agent is configured to weaken a bond of the adhesive layer to the tissue upon exposure to at least one of a plurality of light wavelengths, and
      a polymer light pipe; and
   a blocking layer configured to block the plurality of light wavelengths that activate the at least one release agent.

19. The system of claim 18, wherein the light pipe is one of a pneumatic or fluidic connection tube coupled to a remote therapy device.

20. The system of claim 19, wherein the light pipe is silicone, and wherein the light pipe is flexible.

21. A method comprising:
   coupling the light deactivated adhesive drape system of claim 18 to a patient's tissue;

exposing the photosensitive adhesive layer to the at least one of the plurality of light wavelengths configured to weaken the bond of the adhesive layer; and removing the drape from the tissue.

22. The method of claim 21, further comprising:

sensing a drape state of the drape;

comparing the drape state to a threshold corresponding to a removal state; and determining that the drape state has reached the removal state responsive to a value of the drape state exceeding a value of the threshold.

23. The method of claim 22, further comprising automatically actuating a light source configured to expose the light pipe to the plurality of light wavelengths upon sensing the removal state of the drape.

* * * * *